US006260553B1

(12) United States Patent
Mann

(10) Patent No.: US 6,260,553 B1
(45) Date of Patent: Jul. 17, 2001

(54) INFANT BED HAVING A TILTABLE SLEEPING SURFACE AND METHOD OF TREATING POSITIONAL PLAGIOCEPHALY

(76) Inventor: Robert J. Mann, 2554 Ardmore, SE., Grand Rapids, MI (US) 49506

( * ) Notice: Subject to any disclaimer, the term of this patent is extended or adjusted under 35 U.S.C. 154(b) by 0 days.

(21) Appl. No.: 09/429,423

(22) Filed: Oct. 28, 1999

(51) Int. Cl.[7] .......... A61B 19/00; A61G 7/008

(52) U.S. Cl. .......... 128/898; 128/845; 5/655; 5/733; 5/603; 5/613

(58) Field of Search .......... 5/617, 655, 632, 5/644, 733, 731, 607, 622, 613, 603; 128/845, 846, 898

(56) References Cited

U.S. PATENT DOCUMENTS 1,021,335 3/1912 Robinson et al. .
2,462,579 * 2/1949 Warner .......... 5/733
3,013,281 12/1961 Steiner .
3,462,777 8/1969 Lutsky .......... 5/607
3,795,021 * 3/1974 Moniot .......... 5/644
3,806,110 4/1974 Glasser et al. .
4,962,553 * 10/1990 Marquis .......... 5/731
5,535,464 * 7/1996 Salonica .......... 5/618
5,640,729 6/1997 Mariño .

* cited by examiner

*Primary Examiner*—Alexander Grosz
(74) *Attorney, Agent, or Firm*—Price, Heneveld, Cooper, DeWitt & Litton

(57) ABSTRACT

A method is disclosed for treating/preventing positional plagiocephaly. The method includes the steps of: (a) providing a flat, horizontal first surface and a second surface adjacent the flat surface, the second surface being inclined such that a first side of the second surface is higher than an opposite second side; (b) placing and resting the infant on the first and second surfaces with the infant's head on the second surface and with the infant's shoulders and back on the first surface; (c) after the infant has finished resting, removing the infant from the surfaces; (d) tilting the second surface in an opposite direction such that the first side of the second surface is lower than the second side; (e) when the infant is ready to rest again, placing and resting the infant on the first and second surfaces with the infant's head on the second surface and with the infant's shoulders and back on the first surface; and (f) repeating steps (a) through (e) until the infant reaches an age at which the infant's head is no longer susceptible to positional plagiocephaly. In this manner, the infant sleeps on different sides of its head each time the infant is placed on the surfaces.

11 Claims, 3 Drawing Sheets

INFANT BED HAVING A TILTABLE SLEEPING SURFACE AND METHOD OF TREATING POSITIONAL PLAGIOCEPHALY

BACKGROUND OF THE INVENTION

The present invention generally pertains to beds and mattresses, and more particularly to infant cribs and mattresses. The present invention also relates to a method of treating positional plagiocephaly.

Sudden Infant Death Syndrome (SIDS) is a devastating problem with no known cause. The American Academy of Pediatrics recommended years ago that babies should sleep on their backs on the assumption that part of the SIDS problem might be related to infants suffocating face down in their cribs. The Back to Sleep program began nationwide, and the results have been analyzed. A clear statistical reduction in SIDS deaths occurred after the program was installed.

Some time after the program started, doctors began seeing an increasing number of babies with distorted heads. A number were treated with extensive surgery. Later, it became clear that the distortion, mostly flatness of the back and side of the head, was a direct result of the sleeping position. The weight of the brain on the thin skull bone changes the growth rate, and a progressive deformity occurs for the first four to six months of life. Once infants have a flat spot on their skull, the flatness becomes exacerbated due to the inability of the infants to move their heads once lying on the flat spot due to the general weakness all infants exhibit in their necks.

Historically, several cultures experienced similar positional distortions. The Plains American Indians, by strapping infants to the papoose, caused uniform flatness of the back of the head. The present condition of positional plagiocephaly causes similar skull and neck distortions.

Therapeutic programs to correct the distortion developed, including physical therapy and helmet molding or pressure relief programs. These programs assist some in the correction of the several characteristic shape presentations.

To date, only presumptive circumstances can be used as predictors as to which babies will develop the deformity (large males, twins, and preemies).

SUMMARY OF THE INVENTION

An aspect of the present invention is to provide a method for treating and preventing positional plagiocephaly. The method of the present invention comprises the steps of: (a) providing a flat, horizontal first surface and a second surface adjacent the flat surface, the second surface being inclined such that a first side of the second surface is higher than an opposite second side; (b) placing and resting the infant on the first and second surfaces with the infant's head on the second surface and with the infant's shoulders and back on the first surface; (c) after the infant has finished resting, removing the infant from the surfaces; (d) tilting the second surface in an opposite direction such that the first side of the second surface is lower than the second side; (e) when the infant is ready to rest again, placing and resting the infant on the first and second surfaces with the infant's head on the second surface and with the infant's shoulders and back on the first surface; and (f) repeating steps (a) through (e) until the infant reaches an age at which the infant's head is no longer susceptible to positional plagiocephaly. In this manner, the infant sleeps on different sides of its head each time the infant is placed on the surfaces.

To achieve this method, an infant bed is provided that comprises a flat, horizontal first surface on which to lay the infant's back and shoulders, and means for providing and tilting a second surface on which to lay the infant's head during periods of rest. The means for tilting enables the second surface to be tilted to either of two sides to cause the infant to alternatingly sleep on different sides of its head.

These and other features, advantages, and objects of the present invention will be further understood and appreciated by those skilled in the art by reference to the following specification, claims, and appended drawings.

DETAILED DESCRIPTION OF PREFERRED EMBODIMENTS

As mentioned above and explained in more detail below, the present invention relates to an infant bed and a method of treating, preventing, and reducing the risk of positional plagiocephaly in infants. The method may be practiced using the inventive infant bed. In general, the method involves alternatingly tilting sideways a portion of the mattress surface on which the infant's head is laid, while maintaining the portion of the mattress surface on which the infant's back and shoulders are laid, in a flat, horizontal position. By tilting the portion of the mattress underlying the infant's head sideways, the infant will sleep with its head facing down the slope of the tilted mattress portion. Because the infant generally lacks the muscles to move its head to sleep on the other side of its head against the slope of the mattress, the infant will not sleep on the other side of its head. In this manner, the infant will sleep on one side of its head one night, and sleep on the other side of its head on the next night in a controlled manner. By alternating the side of the infant's head on which the infant sleeps each night (or on some other periodic basis), the infant will not develop the flat spots in its skull that are symptomatic of positional plagiocephaly.

The portion of the mattress surface on which the infant's back and shoulders are laid should be maintained in a generally flat, horizontal orientation. Otherwise, if that portion of the mattress surface is tilted, the infant will tend to roll over on its side or stomach and thus be more susceptible to SIDs. The steps of tilting the head portion of the mattress to different sides every other night should be continued through about the first four to ten months after the infant's due date. Infants that are born premature or are neurologically impaired may be susceptible to a greater age.

The method of the present invention may be implemented using a variety of different means. Broadly speaking, an infant bed constructed in accordance with the present invention comprises a flat, horizontal first surface on which to lay the infant's back and shoulders and means for providing and laterally tilting a second surface on which the infant's head is laid during periods of rest. The tilting means enables the second surface to be tilted to either of two sides.

Figure 9:
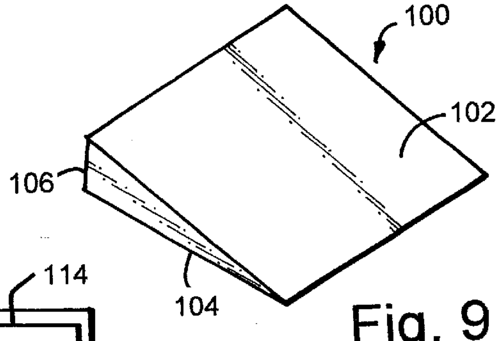
FIG. 9 shows a wedge forming a second embodiment of the present invention.
Figure 11:
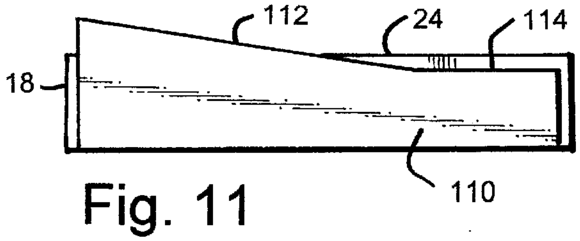
FIG. 11 is a front view of a partially wedge-shaped mattress portion constructed in accordance with a third embodiment of the present invention.
Figure 10:
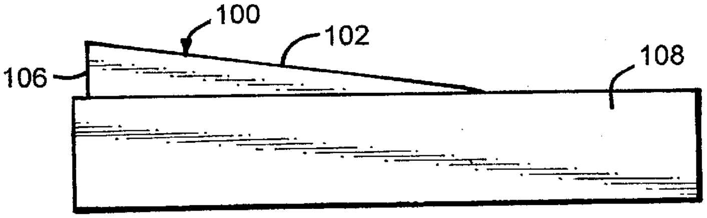
FIG. 10 is a perspective view showing the wedge of FIG. 9 placed on a mattress.

The infant bed may be a crib, cribbette, cradle, bassinet, or any other structure in which an infant may be placed in a generally horizontal position for any extended period of time. An "infant bed," as used and described herein, would not include an adult-sized bed, and therefore, has a sleeping surface length of approximately five feet or less. The means for laterally tilting the portion of the second surface may include structures disposed within the crib mattress, within a box spring, within the mattress support, or in any combination thereof. Alternatively, the tilting means may include a wedge-shaped pillow or foam pad that may be placed on top of a mattress. An example of such a wedge is shown in FIGS. 9–11 and described in detail below. The wedge may be repositioned and reoriented each night to cause the infant to rest its head on opposite sides each night.

Figure 1:
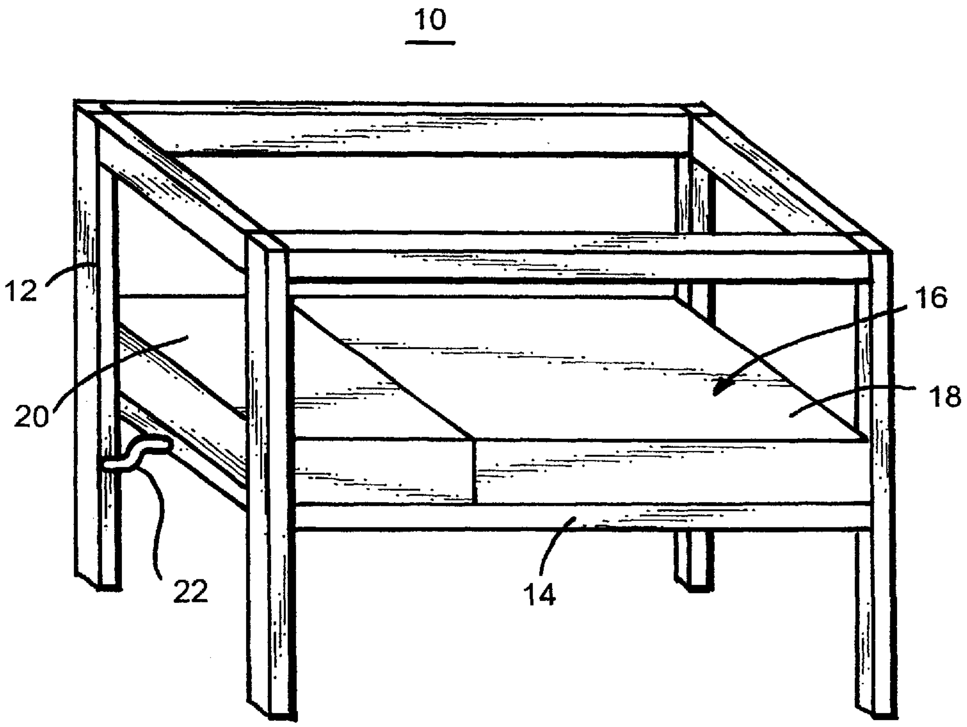
FIG. 1 is a perspective view of an infant crib constructed in accordance with a first embodiment of the present invention.

FIG. 1 shows an infant crib 10 constructed according to a first embodiment. Infant crib 10 is shown in FIG. 1 without the plurality of side spindles that would normally be provided on such a crib, solely for purposes of illustration. It will be appreciated by those skilled in the art that such a crib would include a plurality of vertical spindles spaced equally apart surrounding the crib mattress or other structure to prevent the infant from falling out of the crib. Crib 10 as illustrated includes a frame portion 12 that includes a mattress support frame 14 for supporting a mattress 16. Mattress 16 includes two portions 18 and 20.

Figure 2:
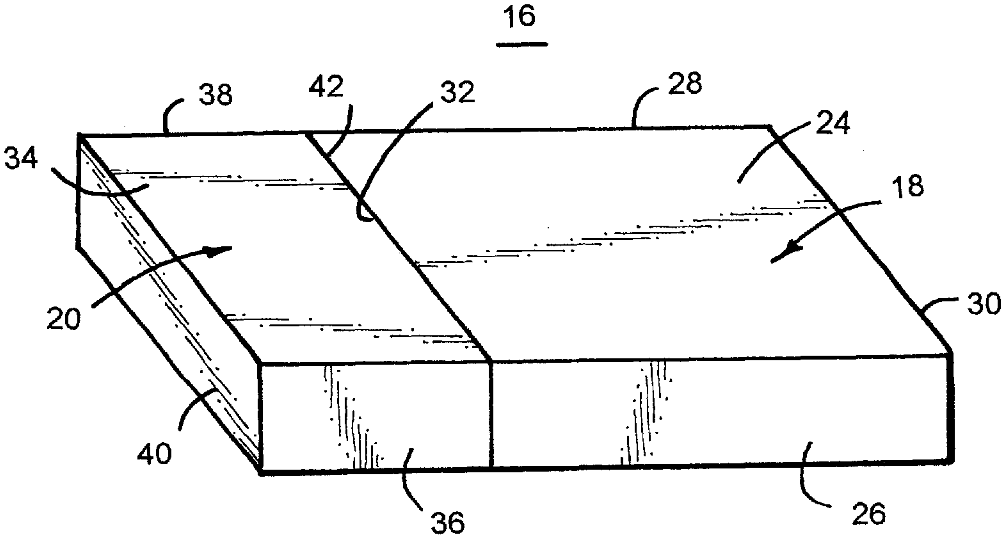
FIG. 2 is a perspective view of a mattress for an infant bed constructed in accordance with a first embodiment of the present invention.

As shown in detail in FIG. 2, first portion 18 (or body portion) of mattress 16 includes a top surface 24 that is bounded by a first side 26, a second side 28 opposite first side 26, a rear end 30, and a front end 32. Second portion 20 (or the head portion) of mattress 16 includes an upper surface 34 that is bounded on all four sides by a first side 36, a second side 38 opposite first side 36, a front end 40, and a rear end 42 that abuts front end 32 of first mattress portion 18. As described further below, mattress portions 18 and 20 are not physically joined unless by means of a mattress cover or sheets, such that head portion 20 of mattress 16 may be pivoted about a longitudinal axis to laterally tilt surface 34 from side to side.

Figure 3:
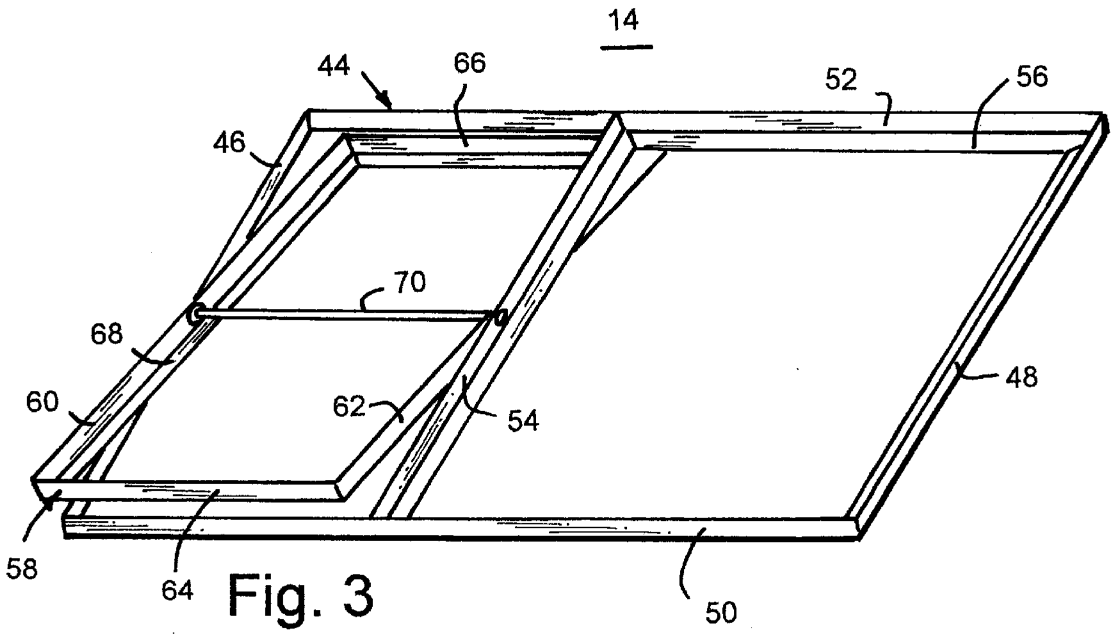
FIG. 3 is a perspective view of a mattress support used in the infant bed shown in FIG. 1.

As shown in FIG. 3, mattress support 14 includes a rectangular mattress frame 44 that extends around the perimeter of mattress 16 and rigidly connects portions of frame 12. Mattress frame 44 includes a front frame member 46, a rear frame member 48, and two side frame members 50 and 52 extending between frame members 46 and 48. Frame members 46–52 are typically vertically oriented steel plates having dimensions slightly larger than the mattress, such that the mattress may fit within mattress frame 44. To support first mattress portion 18, mattress frame 44 further includes a mid-frame member 54 that extends between side frame members 50 and 52 so as to extend vertically upward between mattress portions 18 and 20. Mattress frame 44 further includes a horizontal frame portion 56 that extends horizontally inward from the bottom edge of frame members 48, 50, 52, and 54 so as to provide support for mattress portion 18. As conventional in the art, a plurality of springs or other support beams (not shown) may extend between horizontal frame portions 56 across the area defined by members 48–54 so as to provide sufficient support for mattress portion 18. Alternatively, a box spring may be provided to support mattress 16. In general, mattress support 14 supports first mattress portion 18 such that its upper surface 24 is maintained in a generally flat, horizontal position, as would be the case for a conventional mattress and mattress support assembly.

Figure 6:
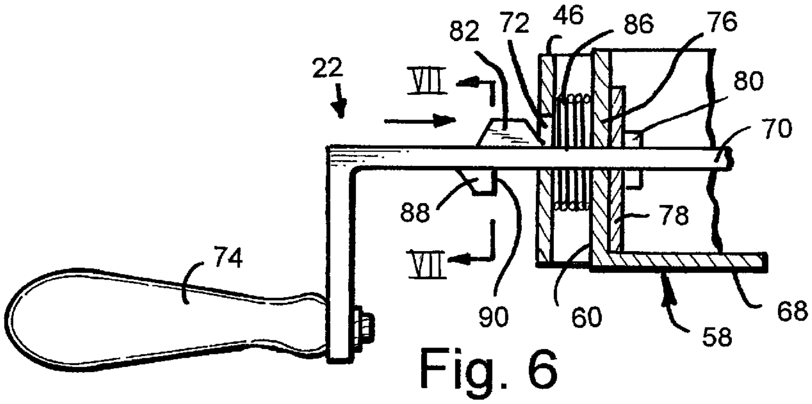
FIG. 6 is a partial cross-sectional view of a turn handle used to tilt a portion of the mattress constructed in accordance with the first embodiment of the present invention.

Mattress support structure 14 differs, however, from a conventional frame structure in that it includes a subframe assembly 58 that is pivotally attached to mattress frame 44 for supporting second mattress portion 20. As shown in FIGS. 3 and 6, subframe assembly 58 includes a front frame member 60, a rear frame member 62, and two side frame members 64 and 66. Frame members 60–66 are arranged as vertical walls and are generally made of steel. Subframe assembly 58 generally has dimensions slightly larger than second mattress portion 20 so as to extend around the lower perimeter of mattress portion 20. Subframe assembly 58 is also dimensioned to be slightly smaller than frame structure 44 so as to fit within an opening defined between front end 46, mid frame member 54, and side frame members 50 and 52. To support mattress portion 20 within subframe assembly 58, a horizontal frame structure 68 is provided that extends inwardly from the lower edges of frame members 60–66.

Subframe assembly 58 is pivotally mounted between front frame member 46 and mid-frame member 54 by means of an axle 70. Axle 70 is generally welded or otherwise secured to subframe assembly 58 while passing through apertures in frame members 46 and 54, such that axle 70 may rotate within those apertures. Axle 70 may also be fixedly attached to a handle 22 so as to allow a person to pivot and tilt mattress portion 20 using handle 22.

Figure 4:
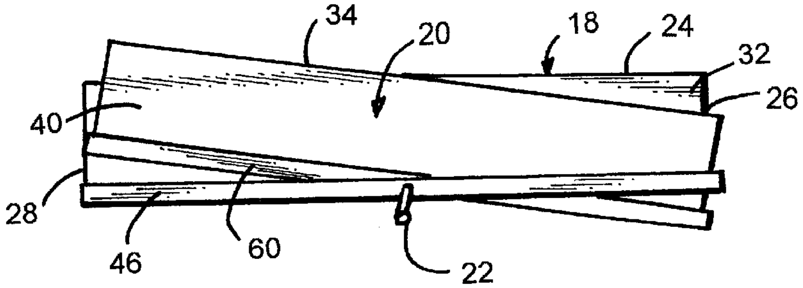
FIG. 4 is a front view of a mattress support and mattress constructed in accordance with a first embodiment of the present invention shown tilted to a first side.
Figure 5:
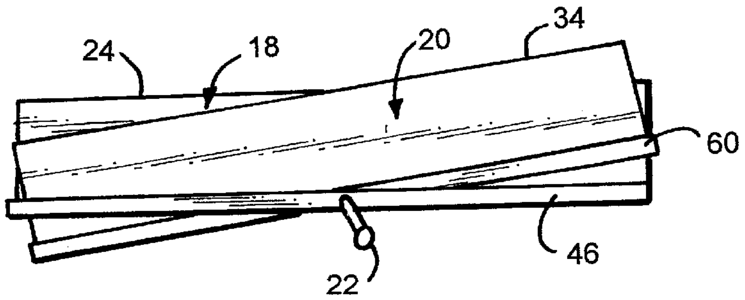
FIG. 5 is a front view of a mattress support and mattress constructed in accordance with a first embodiment of the present invention shown tilted to a second opposite side.

FIGS. 4 and 5 illustrate the manner by which mattress 16 and mattress support 14 may be combined to provide the requisite tilting of a portion of the sleeping surface from side to side that allows the infant's head to be rested on an inclined surface 34 while maintaining the infant's back and shoulders on a flat horizontal surface 24.

Figure 7:
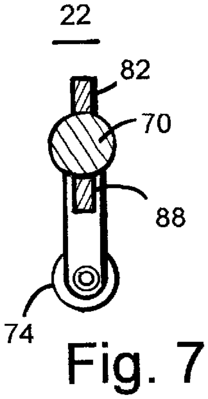
FIG. 7 is a cross-sectional view of the turning handle taken along line VII—VII shown in FIG. 6.
Figure 8:
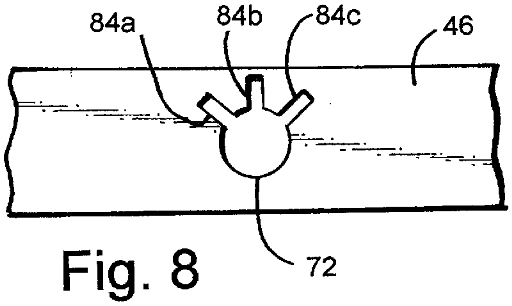
FIG. 8 shows a face plate and aperture for receiving the turn crank shown in FIGS. 6 and 7.

FIG. 6 shows a preferred turn handle structure for mounting handle 22 and subframe assembly 58 within mattress frame 44. As shown in FIGS. 6–8, axle 70 extends through an aperture 72 formed in front frame member 46 and thereafter is bent approximately 90 degrees, such that a handle 74 may be attached. As shown in FIG. 6, axle 70 may be welded or soldered as designated by numeral 76 to front frame member 60 of subframe assembly 58. An additional reinforcement plate 78 or lock nut 80 may be utilized to reinforce the attachment of axle 70 to subframe assembly 58. While axle 70 is generally described as being formed of an elongated cylindrical rod, it will be appreciated that it may have virtually any other shape. As described below, however, it is preferable that axle 70 is at least round in cross section near the end that passes through aperture 72 in front frame member 46 so as to allow rotation of axle 70 within aperture 72.

To allow subframe assembly 56 to be moved and then locked into a tilted position, a fin 82 extends radially outward from a portion of axle 70 for fitting within and engaging respective key slots 84*a*–84*c*. As best illustrated in FIG. 8, one key slot 84*b* would extend vertically upward without inclination, which would represent the key slot in which fin 82 should be inserted to maintain subframe assembly 58 in a level horizontal position, whereas key slots 84*a* and 84*c* are inclined such that when fin 82 is slid into one of these key slots, subframe assembly 58 is tilted into one of the respective positions shown in FIGS. 4 and 5. With fin 82 firmly secured within one of slots 84*a*–84*c*, subframe assembly 58 and mattress portion 20 will be locked in a level or tilted position.

To allow fin 82 to be moved between slots 84*a*–84*c* while preventing accidental unlocking of the position of subframe assembly 58, a compression spring 86 may be provided around rod 70 in between front frame member 46 of mattress frame 44 and front frame member 60 of subframe assembly 58. This compression spring biases frame members 46 and 60 apart, thereby drawing fin 82 towards the front surface of frame member 46 so as to pull fin 82 within one of slots 84*a*–84*c* when aligned therewith. To limit the distance in which fin 82 extends through or past front frame member 46, a second fin 88 having a flat surface 90 is provided in an opposite side of axle 70 than fin 82 so as to be pulled against the front surface of front frame member 46 and thereby keep axle 70 from extending too far past front frame member 46. Compression spring 86 should therefore have sufficient compressive force to securely hold fin 82 within one of slots 84*a*–84*c* while nevertheless allowing a person to grasp handle 74 and exert a sufficient pulling force to pull fin 82 far enough outside one of key slots 84*a*–84*c* and rotate the handle such that fin 82 will fit within a different one of slots 84*a*–84*c*.

Although the first embodiment has been described as using a single handle and axle to simultaneously tilt one side of second mattress portion 20 up/down while tilting the other side down/up, it will be appreciated that subframe assembly 58 could be hinged or separated into two side portions and separate handles and axles or other mechanisms could be provided to independently tilt upwards the two sides of second mattress portion 20. Additionally, virtually any known mechanism for laterally tilting a mattress may be used to tilt second mattress portion 20. See, for example, U.S. Pat. Nos. 1,021,335; 3,013,281; 3,462,777; and 5,640,729, which disclose various mechanisms for laterally tilting all or most of a mattress or sleeping surface used for adults.

FIGS. 9 and 10 illustrate a second embodiment of the present invention. According to this embodiment, a foam wedge 100 having an inclined surface 102, a bottom surface 104, and a side surface 106 is placed on top of a conventional mattress 108. Thus, as illustrated in FIG. 10, the wedge may provide an inclined surface similar to the inclined surface provided by the second mattress portion 20 of the first embodiment. To change the direction in which surface 102 is tilted, one would simply pick up wedge 100 and align side surface 106 with the other side surface of conventional mattress 108. Wedge 100 should have surface 102 inclined at such an angle that makes it difficult for an infant to turn its head once laid with the side of its head on inclined surface 102. Wedge 100 should have a width that extends more than half the width of mattress 108 to ensure the infant does not slide down the inclined surface 102 off of wedge 100 and onto the flat portion of mattress 108. On the other hand, wedge 100 cannot be so wide as to provide too large of a distance between the thickest portion of wedge 100 and the upper surface of mattress 108.

Wedge 100 offers the advantage that the structure of the infant bed need not be modified to provide the advantages of the invention and allow for the practice of the inventive method. Further, wedge 100 may be picked up and moved to any infant bed or other structure in which the infant may be placed for resting.

FIG. 11 shows a third embodiment of the present invention. As illustrated, this mattress structure includes a first mattress portion 18 similar to that used in the first embodiment, which has a flat upper surface 24 that is maintained in a generally flat horizontal position. In place of second portion 20, which is otherwise a flat mattress portion, a wedge-shaped mattress portion 110 may be utilized. Such a structure could be used in a conventional infant crib without modification to the mattress support structure. In this case, the wedge-shaped portion 110 may simply be reoriented every night, such that its inclined surface 112 is inclined to opposite sides each night. As shown in FIG. 11, the wedge-shaped mattress portion 110 may have a flat upper surface portion 114 on one side so as to prevent the distance between upper surface 24 and the upper surface of wedge-shaped mattress portion 110 from becoming too great near the side edges. A similar flat surface could be provided at the other end again to reduce the surface height differential between the mattress portions.

Although the structures used to serve as the means for providing and tilting a sleeping surface on which an infant's head is laid have been illustrated and described as manually manipulated structures, it will be appreciated that an automated system could be provided utilizing an electrical motor or the like to automatically tilt the sleeping surface for the infant's head. Using such automated means would allow the tilted surface to be tilted to different sides at periodic intervals throughout a single night. Alternatively, such automated means could be programmed to automatically tilt the bed surface portion to different sides each night so that the parent or guardian of the infant would not have to remember to reposition the tilting mechanism each night.

The above description is considered that of the preferred embodiments only. Modifications of the invention will occur to those skilled in the art and to those who make or use the invention. Therefore, it is understood that the embodiments shown in the drawings and described above are merely for illustrative purposes and not intended to limit the scope of the invention, which is defined by the following claims as interpreted according to the principles of patent law, including the doctrine of equivalents.

The invention claimed is:

1. A physical therapy method for treating/preventing positional plagiocephaly in an infant, the method comprising the steps of:

(a) providing a flat, horizontal first surface and a second surface adjacent the flat surface, the second surface being inclined such that a first side of the second surface is higher than an opposite second side;

(b) placing and resting the infant on the first and second surfaces with the infant's head on the second surface and with the infant's shoulders and back on the first surface;

(c) after the infant has finished resting, removing the infant from the surfaces;

(d) tilting the second surface in an opposite direction such that the first side of the second surface is lower than the second side;

(e) when the infant is ready to rest again, placing and resting the infant on the first and second surfaces with the infant's head on the second surface and with the infant's shoulders and back on the first surface; and (f) repeating steps (a) through (e) until the infant reaches an age at which the infant's head is no longer susceptible to positional plagiocephaly.

2. The method of claim 1, wherein step (a) includes providing a flat, horizontal mattress serving as said first surface.

3. The method of claim 2, wherein step (a) includes providing a foam wedge on top of a portion of said mattress such that an upper surface thereof is inclined towards a first side of a said mattress to serve as said second surface.

4. The method of claim 3, wherein step (d) includes repositioning said foam wedge such that an upper surface of said wedge is inclined to a second side of said mattress that is opposite said first side of said mattress.

5. The method of claim 1, wherein step (a) includes providing a first mattress that is shorter in length than a bed frame that supports said first mattress, an upper surface of said first mattress serves as said first surface.

6. The method of claim 5, wherein step (a) includes providing a foam structure having an inclined upper surface within the bed frame adjacent to one end of said first mattress.

7. The method of claim 6, wherein step (d) includes repositioning said foam structure at the end of said first mattress such that the inclined surface is tilted to the opposite side.

8. The method of claim 5, wherein step (a) further includes providing a second mattress that may be laterally tilted from side to side, an upper surface of said second mattress serves as said second surface.

9. The method of claim 1, wherein the infant's head is no longer susceptible to positional plagiocephaly after about four months.

10. The method of claim 1, wherein the infant's head is no longer susceptible to positional plagiocephaly after about ten months after the infant's due date.

11. A physical therapy method for treating/preventing positional plagiocephaly in an infant, while maintaining the torso of the infant in a generally horizontal position, comprising the steps of:

(a) tilting a portion of a sleeping surface upon which the infant's head lies to a first side;

(b) placing the infant on the sleeping surface with the infant's head on said portion of the sleep surface during times that the infant is resting;

(c) tilting said portion of the sleeping surface to a second side opposite said first side;

(d) placing the infant on the sleeping surface with the infant's head on said portion of the mattress during times that the infant is resting; and (e) repeating steps (a) through (d) until the infant's head is no longer susceptible to positional plagiocephaly.

* * * * *